United States Patent [19]

Saute

[11] 4,126,142
[45] Nov. 21, 1978

[54] FACE MASK

[76] Inventor: Robert E. Saute, 10236 Mossy Rock Cir., Los Angeles, Calif. 90024

[21] Appl. No.: 789,217

[22] Filed: Apr. 20, 1977

[51] Int. Cl.² .............................................. A45D 7/00
[52] U.S. Cl. ....................................................... 132/7
[58] Field of Search ........................ 132/7; 424/78, 71

[56] References Cited

U.S. PATENT DOCUMENTS

| | | | |
|---|---|---|---|
| 3,523,998 | 8/1970 | Feinstone | 424/78 |
| 3,862,309 | 1/1975 | Krochock | 424/78 |
| 3,937,802 | 2/1976 | Fujimoto | 424/71 |

Primary Examiner—G.E. McNeill
Attorney, Agent, or Firm—Kenneth J. Hovet

[57] ABSTRACT

A two-stage skin treating technique wherein a film of sodium polystyrene sulfonate cosmetic solution is applied to predetermined areas of the skin and allowed to dry. The dried film tightens the skin and enhances blood circulation which causes an increase in subcutaneous fluids and diminishes skin lines. When the film is removed, scurf skin and sebaceous soil is also removed thereby creating a highly effective cleansing action. A moisture barrier formulation is subsequently applied to enhance and protect the skin moisture level while creating a fresh youthful appearance and feeling.

5 Claims, No Drawings

FACE MASK

BACKGROUND OF THE INVENTION

1. Field of the Invention

The present invention relates to cosmetic techniques and, more particularly, to methods and compositions for cosmetic treatment of the skin.

2. Description of the Prior Art

In general, two broad categories of treatments have evolved for beautifying one's skin. Among the first category are creams, astringents and lotions which are massaged into the skin. A second category includes powders or coatings which are used to mask or cover portions of the skin. U.S. Pat. No. 3,862,309 is representative of the latter group wherein a composition is disclosed which is left on the skin to smoothout and/or mask wrinkles. The composition contains a small percentage of high molecular weight sodium polystyrene sulfonate and may include color pigments when functioning as a makeup.

The above-patented treatment is unlike the present invention because it relies on the presence of a skin covering to mask one's skin. The system described herein provides a natural two-stage skin treatment whereby the skin is cleansed and plumped by the application and removal of a low molecular weight sodium polystyrene sulfonate-based film followed by the application of a cosmetic oil composition. The present system is not dependent on the durability or strong adherence of a film over skin nor is it concerned with skin remolding by external means.

SUMMARY OF THE INVENTION

In accordance with the present invention, there is provided a novel cosmetic skin treating system which cleanses the skin and diminishes wrinkles without the necessity of a user wearing a tight adherent skin cover. The system utilizes a 2–25 weight percent aqueous solution of sodium polystyrene sulfonate having a molecular weight below about 200,000. The solution is applied to one's skin and allowed to dry. It is then removed and a moisture barrier preparation applied. The combined treatment produces a natural long-lasting youthful skin appearance which is not attainable with an oil or cleansing lotion treatment alone.

DESCRIPTION OF THE PREFERRED EMBODIMENTS

The skin treating formulations used in the process of this invention comprise aqueous solutions of polystyrene sulfonate salts which contain effective amounts of a viscolizer and a liquid modifier defined as a plasticizer and/or surfactant depending on the specific end product desired. Additional additives may be used for obtaining particular effects such as preservatives, volatile solvents, humectants, fragrances and dermotrophic agents.

In general, the polystyrene sulfonate salt should be present in a concentration ranging from about 2–25 percent by weight of the total aqueous composition with the liquid modifier and viscolizer each being present in amounts ranging between about 0.1–20 weight percent.

The sulfonated polystyrene salts useful in the practice of this invention have molecular weights less than about 200,000 and are produced by sulfonating styrene polymers and treating the product with neutralizing bases such as sodium hydroxide, ammonium hydroxide, potassium hydroxide or sodium carbonate. Sodium salts of the sulfonated polymers are preferred.

In general, the basic oil formulation of the present invention may comprise any one or combination of animal, vegetable or mineral oils to achieve the desired effect of forming a barrier to prevent tissue moisture loss. Mineral oil may be used as the main barrier as well as vegetable oils such as soybean oil, castor oil, avocado, corn and the highly unsaturated oils such as safflower oil, olive oil, rice bran oil and peanut oil. Synthetic esters such as isopropyl myristate, octyl stearate, dioctyl adipate are useful as well as porosity esters such as 2-ethyl hexyl stearate and 2-ethyl hexyl palmitate which are miscible with mineral and vegetable oils. Other additives such as oil soluble proteins and vitamins such as A, D and E can be added to enhance the cosmetic effects of the oil formulas. Various animal derived oils such as mink oil may be used also.

Liquid modifiers such as plasticizers and/or surfactants which are useful in conjunction with the present invention may be characterized as anionic, cationic, nonionic and amphoteric compounds suitable for physiological use. Representative of such compounds are silicone fluids, water soluble polyoxyethylene fatty ethers, propylene glycol, polysorbate 20 and 80, glycerin, sorbitol, and acetylated esters of the ethoxylated ether of lanolin alcohols. These materials are used to adjust the spreading ability of the film solutions. They also facilitate removal of the dried film. Other compounds useful for the above purposes are imidazoline type zwitter ions and betaines.

Viscolizers suitable for use in controlling the viscosity of the sulfonated polystyrene solutions are natural gums such as tragacanth, acacia, guar, gelatin, pectin, carrageenan, sodium alginate and dextrin. Synthetic gums such as methyl cellulose, carboxymethylcellulose, polyvinylpyrrolidone, polyvinylpyrrolidone/vinyl alcohol copolymer, polymers of acrylic acid (carboxy vinyl polymers), polyvinyl alcohol, and vinyl pyrrolidone/vinyl acetate copolymer are also useful.

The drying time of the films can be shortened by the addition of volatile solvents such as alcohol, e.g. denatured ethanol. Conversely, the drying time can be increased with the addition of small amounts of glycerin or other humectants. The inclusion of a small amount of preservative or physiological bactericides in the film solutions may be appropriate to prevent microbial growth. Suitable physiological bactericides are methyl parahydroxybenzoate and other parahydroxybenzoic acid esters, formaldehyde, imidazolidinyl urea, quaterninum-15, sorbic acid, and 2-bromo-2-nitropropane, 1,3-diol quaternary ammonium salts and formaldehyde donners.

A wide variety of optional dermotrophic agents can be incorporated in the film solution to create certain desirable effects on the skin. Peripheral vasodialators such as methyl salicylate and nicotinic acid and its esters can be incorporated in the film composition. Examples of herbal additives are Azulene, Chamomile flowers, Witch hazel leaves, Arnica flowers. Other agents that can be used are powdered milk, proteolytic enzymes, urea, egg oil, egg powder, avocado powder, modified starches, bentonites, clays, ichthammol, vitamins such as vitamins A, B, C, D and E, vegetable extracts and amino acids, polypeptides and proteins. Certain polyvalent metals such as aluminum chloride might be used to produce an astringent effect. Small quantities of cationics such as dimethyl-aminopropyl lanolin (acid) amide diethosulfate quaternium may be used as a "skin feel" agent.

The invention will now be illustrated by the following specific examples, but it is intended that the invention shall not be limited thereby.

EXAMPLES

Each of the skin formulations are prepared in substantially the same manner. The viscolizers are added to cold water. With constant stirring, the water is heated to 175° F. and the polystyrene sulfonate salt is added. While the solution is allowed to cool, the plasticizers, surfactants, preservatives and other desired ingredients are added. When the temperature reaches about 90° F., the volatile materials are added such as solvents and fragrances. The pH is adjusted to a range between 3.5 to 8.0 and optional colorants are added to the desired shade.

EXAMPLE 1

| Skin Formulation: | Weight Percent |
| --- | --- |
| Polystyrene sulfonate salt | 15.0 |
| Carrageenan | 1.0 |
| Alpine herbs | 2.0 |
| Polysorbate 80 | 0.5 |
| Alcohol | 5.0 |
| Germall 115 | 1.0 |
| Water | 75.5 |

The formulation is prepared as described above and applied to one's skin by brushing or dabbing with cotton pads to form an even film thereover. The film is allowed to dry under ambient conditions for 10 to 45 minutes. A cool water rinse is used to remove the film and the area covered by the film is treated immediately with an oil formulation as follows:

| | Weight Percent |
| --- | --- |
| Wickenol 163 | 55.0 |
| Castor oil | 18.55 |
| Avocado oil | 10.0 |
| Camellia oil | 10.0 |
| Vitamin E Natural 1100 | 3.0 |
| Lecithin | 2.0 |
| Isostearic Hydrolyzed animal protein | 1.0 |
| Vitamin A & D | 0.33 |
| Butyl paraben | 0.1 |
| Mixed tocopherols | 0.02 |
| Fragrance | q.s. |

EXAMPLE 2

Example 1 was repeated with the following compositions:

| | Weight Percent |
| --- | --- |
| Skin Formulation: | |
| Polystyrene sulfonate salt | 12.0 |
| Hydrolyzed collagen protein | 3.0 |
| Polysorbate 20 | 1.0 |
| Glycerin | 2.0 |
| Dowacil 200 | 0.1 |
| Fragrance | 0.2 |
| Citric Acid | q.s. pH5.5 |
| Water | 81.7 |
| Oil Formulation | |
| Mineral oil | 60.0 |
| Isopropyl myristate | 20.0 |
| Butyl paraben | 0.1 |
| Avocado oil | 19.9 |

EXAMPLE 3

Example 1 was repeated with the following:

| | Weight Percent |
| --- | --- |
| Skin Formulation: | |
| Polystyrene sulfonate salt | 5.0 |
| Carbopol 910 | 1.0 |
| Polysorbate 20 | 1.0 |
| Carbowax 200 | 2.0 |
| Aloe Vera 200 | 1.0 |
| F.D.&C. Blue No. 1 | 0.01 |
| Fragrance | 0.30 |
| Methyl paraben | 0.10 |
| Propyl paraben | 0.05 |
| Germall 115 | 0.10 |
| Water | 86.40 |
| Poly vinyl alcohol | 3.04 |
| Oil Formulation: | |
| Isopropyl palmitate | 80.0 |
| Safflower oil | 15.0 |
| Butyl paraben | 0.1 |
| Vitamin E Natural | .9 |
| Corn oil | 4.0 |

EXAMPLE 4

Example 1 was repeated with the following:

| | Weight Percent |
| --- | --- |
| Skin Formulation: | |
| Polystyrene sulfonate salt | 22.50 |
| Vitamin E | 0.10 |
| Vitamin A & D | 0.10 |
| Vitamin B Complex | 0.50 |
| Amphoteric -6 | 2.0 |
| Bronopol | 0.1 |
| Fragrance | 0.5 |
| Color | q.s. |
| Water | 74.2 |
| Oil Formulation: | |
| Mink oil | 40.0 |
| Sesame oil | 40.0 |
| Buyl paraben | 0.2 |
| Dioctyl adipate | 19.5 |
| Perfume | 0.3 |

EXAMPLE 5

Example 1 was repeated with the following:

| | Weight Percent |
| --- | --- |
| Skin Formulation: | |
| Polystyrene sulfonate salt | 15.0 |
| Nicotinic acid | 0.25 |
| Carbowax 400 | 3.0 |
| Baureth-23 | 2.0 |
| Fragrance | 0.5 |
| Germall 115 | 1.0 |
| Color | q.s. |
| Water | 78.25 |
| Oil Formulation: | |
| 2-ethyl hexyl stearate | 10.0 |
| 2-ethyl hexyl palmitate | 10.0 |
| di (2-ethyl hexyl) adipate | 20.0 |
| Mineral oil | 40.0 |
| Isopropyl Myristate | 15.0 |
| Butyl paraben | 0.1 |
| Perfume | 0.1 |
| Camellia oil | 4.8 |

Skin treated in accordance with the above was cleansed and refreshened. Half face tests resulted in visual natural plumping of the skin and substantial diminution of skin lines. The test subjects reported a fresh youthful appearance not attainable with available lotions or face masks.

What is claimed is:

1. A skin treatment for diminishing wrinkles by plumping the skin and maintaining the skin in a plumped state comprising:
preparing an aqueous solution which includes about 2–25 weight percent polystyrene sulfonate salt having a molecular weight of less than 200,000;
about 1–20 weight percent liquid modifiers suitable for physiological use selected from the group consisting of anionic, cationic, nonionic and amphoteric plasticizers and surfactants;
about 1–20 weight percent viscolizer selected from the group consisting of natural gums, synthetic gums and vinyl polymers;
applying a thin film of said aqueous solution to one's skin;
allowing said film to dry and tighten the skin causing a plumping of the skin tissue;
removing said film; and,
immediately thereafter forming a moisture barrier over at least the skin previously covered by said film to maintain the skin in a plumped state by applying to said skin a cosmetic oil composition selected from the group consisting of animal oil, vegetable oil, mineral oil, and synthetic esters.

2. The treatment of claim 1 wherein said sulfonate salt is sodium polystyrene sulfonate.

3. The treatment of claim 2 wherein said modifiers are selected from silicone, polyoxyethylated fatty ethers, propylene glycol, polysorbate 80, glycerin, sorbitol, acetylated esters of ethoxylated ether of lanolin alcohols, imidazoline type zwitter ions and betaines.

4. The treatment of claim 2 wherein said viscolizer is selected from tragacanth, acacia, guar, gelatin, pectin, carrageenan, sodium alginate and dextrin, methyl cellulose, carboxymethylcellulose, polyvinylpyrrolidone, polyvinylpyrrolidone/vinyl alcohol copolymer, polymers of acrylic acid, carboxy vinyl polymers, polyvinyl alcohol, and vinyl pyrrolidone/vinyl acetate copolymer.

5. The treatment of claim 1 wherein said solution has a pH between about 3.5 and 8.0.

* * * * *